United States Patent [19]

Fischer

[11] Patent Number: Plant 6,639

[45] Date of Patent: Feb. 28, 1989

[54] AFRICAN VIOLET PLANT NAMED PICOTEE RUFFLES

[76] Inventor: Arnold Fischer, Kahlendamm 22, 3000 Hanover 51, Fed. Rep. of Germany

[21] Appl. No.: 85,090

[22] Filed: Aug. 13, 1987

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A cultivar of African violet named Picotee Ruffles, characterized by its large single bi-colored flowers which have ruffled edges and are mainly white with a dark purple picotee; medium green ruffled leaves, compact growth habit, and its floriferousness.

1 Drawing Sheet

The present invention comprises a new and distinct cultivar of African violet plant, botanically known as *Saintpaulia ionantha,* named Picotee Ruffles.

The new cultivar is a product of a planned breeding program carried out by applicant in Hannover, Federal Republic of Germany. The basic objective of the breeding program was to create a new African violet cultivar having single purple and white bi-color flowers, ruffled petals and foliage, high flower productivity and compact growth habit.

The new cultivar was originated from a cross made by applicant in the controlled breeding program. Both the female (or seed) and the male (or pollen) parents were unnamed seedlings not specifically identifiable.

Picotee Ruffles was discovered and selected by applicant as a flowering plant within the progeny of the stated cross in a controlled environment in Hannover, Federal Republic of Germany. Asexual reproduction of the new cultivar by leaf cuttings, as performed by me at Hannover, Federal Republic of Germany, has demonstrated that the combination of characteristics as herein disclosed for the new cultivar are firmly fixed and retained through successive generations of asexual reproduction.

Picotee Ruffles has not been observed under all possible environmental conditions. The phenotype may vary significantly with variations in environment such as temperature, light intensity and day length. The following observations, measurements and values describe the new cultivar as grown in Parrish, Fla. under greenhouse conditions which closely approximate those generally used in commercial practice.

The following traits have been repeatedly observed and are determined to be basic characteristics of Picotee Ruffles which in combination distinguish this African violet as a new and distinct cultivar:

(1) Large single zygomorphic rotate flowers with ruffled margins and 32–36 mm in diameter.

(2) Flowers are bi-colored with a white background and a purple edge or picotee. The margins are very ruffled.

(3) Medium green, pubescent foliage, oval shaped with ruffled sinuate margins, cordate base and a very broadly acute apex.

(4) Compact rosette habit with flowers held erect on strong, upright peduncles.

(5) Very floriferous, with flowers continuing to open for many weeks after the onset of flowering.

(6) Suitable for production in 10 cm pots, finishing in 9–13 weeks when started from a 2¼" plantlet.

The new cultivar is most similar to the cultivar Fairy Queen, disclosed in U.S. Plant Pat. No. 4,935. Picotee Ruffles is principally distinguished from Fairy Queen by its less ruffled leaves and its purple edge or picotee. The color of the picotee of Fairy Queen is rose.

The accompanying photographic drawing shows a typical specimen plant of the new cultivar. The photograph is in black and white, with a single flower being colored to accurately depict the true flower colors designated below by color values.

In the following description, color references are made to The Royal Horticultural Society Colour Chart (R.H.S.), except where general colors of ordinary significance are referred to. Color values were taken under fluorescent light conditions at approximately 4:00 p.m. in Parrish, Fla.

Botanical classification: *Saintpaulia ionantha,* Ramat., cv. Picotee Ruffles.

Parentage: Unknown.

Propagation: The new cultivar holds its distinguishing characteristics through successive propagations by leaf cuttings.

Plant: From 5 cm to 10 cm tall when grown in pots, and approximately 20 cm in diameter when fully grown. The growth rate is vigorous, and the general shape of the fully grown plant is round.

*Leaves.*—Quantity: Abundant. Shape: Oval with ruffled sinuate margins. Diameter: Up to 8 cm for a mature leaf. Texture: Pubescent, glossy. Ribs and Veins: Pinnate. Color (upper side): 137 A. Color (under side): 138 D. Petioles: Light green.

*Flowers.*—Buds: Size: About 1 cm×1 cm. Shape: Round. Rate of opening: Normal. Sepals: Shape: Lanceolate. Color: Light green. Phyllaries: 2, lanceolate. Color: 137 A. Calyx: Shape: Funnel. Size: About 1 cm in diameter. Aspect: Pubescent. Peduncle: Length: Up to 8 cm. Character: Erect, rigid. Color: Light green.

*Individual flowers.*—Number of petals: 5. Size: Approximately 33 mm in diameter and 10 mm deep. Shape: Cup shaped when bloom first opens, becoming flat as bloom matures. Color (upper side): Background color clear white, picotee 83 A and B. Color (under side): White and 83 C and D. Flowers fade slightly as they age. The flower color may vary somewhat depending upon the amount of light, fertilizer, temperature and other growing conditions. Borne: Cymose clusters on upright peduncles, up to 8 cm long. Flowering habit: Flowers profusely and intermittently year round, with blooms lasting 2–3 weeks after which petals dry up but do not drop. Finishes in 9–12 weeks when a $2\frac{1}{4}''$ plantlet is placed in a 10 cm pot.

*Reproductive organs.*—Stamens: Stamens borne singly on one side of ovary. 2 anthers basifixed. Anthers: 2 mm×2 mm, yellow. Filaments: 2 mm, white with purple streaks. Pollen color: Yellow.

Pistels: Number: 1. Styles: 1, 6–8 mm long. Stigma: Sticky, white. Ovaries: Superior.

*Roots.*—Fibrous and fine.

Disease resistance: No African violet diseases observed to date.

I claim:

1. A new and distinct cultivar of African violet named Picotee Ruffles, as illustrated and described, and particularly characterized by its large single bi-colored flowers which have ruffled edges and are mainly white with a dark purple picotee; medium green ruffled leaves, compact growth habit, and its floriferousness.

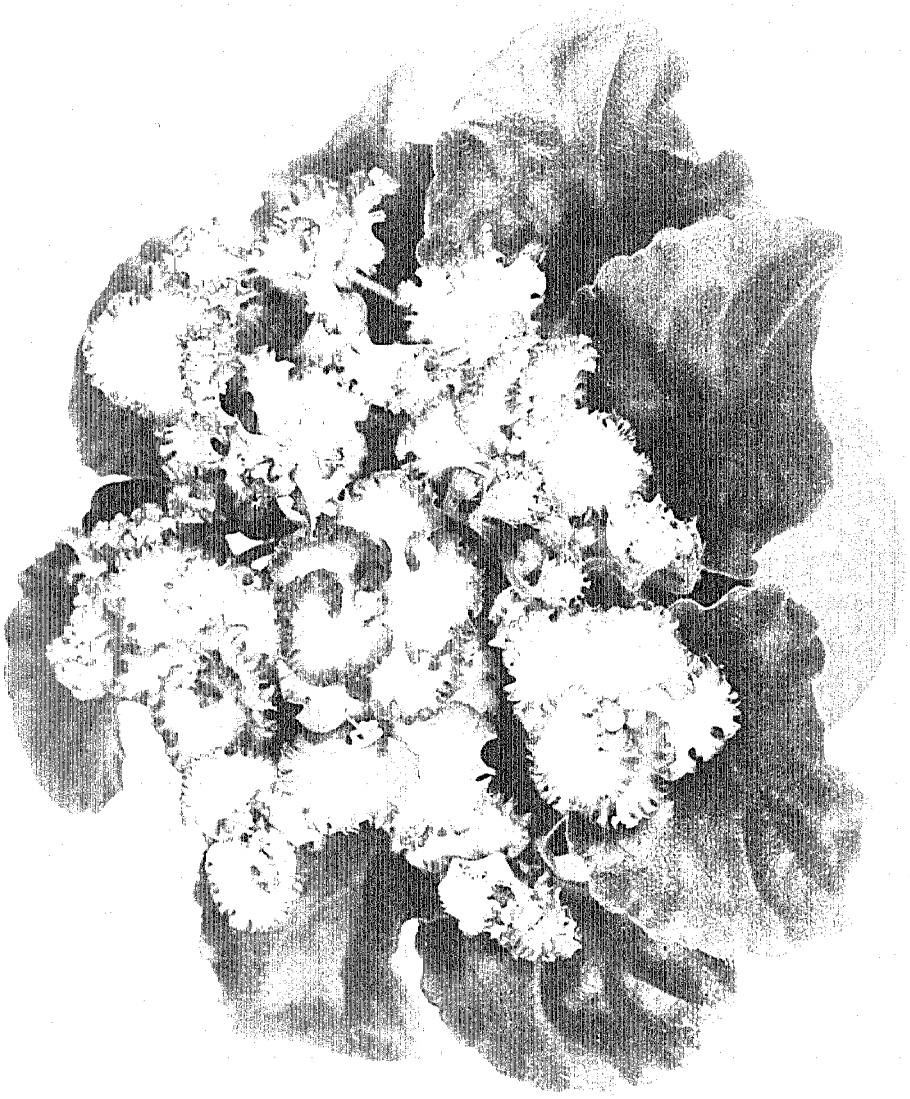

* * * * *